US009638665B2

(12) United States Patent
Gorbunov

(10) Patent No.: US 9,638,665 B2
(45) Date of Patent: May 2, 2017

(54) METHOD FOR OBTAINING AEROSOL PARTICLE SIZE DISTRIBUTIONS

(71) Applicant: PARTICLE MEASURING SYSTEMS, INC., Boulder, CO (US)

(72) Inventor: Boris Zachar Gorbunov, Kent (GB)

(73) Assignee: PARTICLE MEASURING SYSTEMS, INC., Boulder, CO (US)

( * ) Notice: Subject to any disclaimer, the term of this patent is extended or adjusted under 35 U.S.C. 154(b) by 0 days.

(21) Appl. No.: 14/898,934

(22) PCT Filed: Jun. 17, 2014

(86) PCT No.: PCT/EP2014/062761
§ 371 (c)(1),
(2) Date: Dec. 16, 2015

(87) PCT Pub. No.: WO2014/202632
PCT Pub. Date: Dec. 24, 2014

(65) Prior Publication Data
US 2016/0370320 A1    Dec. 22, 2016

(30) Foreign Application Priority Data

Jun. 17, 2013 (GB) .................................. 1310759.4

(51) Int. Cl.
*G01N 15/10* (2006.01)
*G01N 15/02* (2006.01)
*G01N 27/62* (2006.01)

(52) U.S. Cl.
CPC ....... *G01N 27/622* (2013.01); *G01N 15/0266* (2013.01); *G01N 15/10* (2013.01); *G01N 2015/1087* (2013.01)

(58) Field of Classification Search
CPC ... G01N 27/622; G01N 15/0266; G01N 15/10
See application file for complete search history.

(56) References Cited

U.S. PATENT DOCUMENTS 5,922,976 A    7/1999   Russell et al.
6,003,389 A    12/1999  Flagan et al.
(Continued)

FOREIGN PATENT DOCUMENTS

| EP | 1965191 A1 | 9/2008 |
| JP | 2004053511 A | 2/2004 |
| WO | 03041114 A2 | 5/2003 |

OTHER PUBLICATIONS

International Search Report for PCT/EP2014/062761 dated Oct. 17, 2014.
(Continued)

*Primary Examiner* — Nicole Ippolito
*Assistant Examiner* — Sean Luck
(74) *Attorney, Agent, or Firm* — Heslin Rothenberg Farley & Mesiti P.C.

(57) ABSTRACT

The invention provides a method for obtaining aerosol particle size distributions with a scanning mobility particle sizer (SMPS) device comprising a differential mobility analyzer (DMA); which method comprises the stages:

(i) collecting a first data set of particle concentrations vs. size for a size range from a predetermined minimal size $D_{min}$ to an intermediate size $D_t$ by varying a voltage applied to a DMA column of an SMPS from $V_{min}$ to $V_{t1}$ at a first sheath flow rate $Q_{sh1}$;

(ii) changing the sheath flow rate from the first sheath flow rate $Q_{sh1}$ to a second sheath flow rate $Q_{sh2}$;

(iii) collecting a second data set of particle concentrations vs. size for a size range from the intermediate size $D_t$ to a predetermined maximum size $D_{max}$ by varying the voltage applied to the DMA column of the SMPS from $V_{t2}$ to $V_{max}$ at the second sheath flow rate $Q_{sh2}$;

(iv) convolving the first data set from stage (i) using an apparatus function of the DMA and the sheath flow rates $Q_{sh1}$ and $Q_{sh2}$ in stage (ii);

(Continued)

(v) combining the convolved data set from stage (iv) with the second data set from stage (iii) to form a merged data set corresponding to the size distribution from $D_{min}$ to $D_{max}$; and
(vi) deconvolving the merged data set to provide a size distribution for the full size range $D_{min}$ to $D_{max}$.

Also provided are a DMA, SMPS or Fast Mobility Particle Sizer (FMPS) apparatus set up to perform the method.

8 Claims, 9 Drawing Sheets

(56)　　　　　　References Cited

U.S. PATENT DOCUMENTS

| | | | | |
|---|---|---|---|---|
| 6,259,101 | B1 * | 7/2001 | Wexler | G01N 21/718 |
| | | | | 250/287 |
| 8,301,396 | B1 * | 10/2012 | Dhanijala | G01N 15/0266 |
| | | | | 702/24 |
| 2004/0025567 | A1 | 2/2004 | Marjamaki et al. | |
| 2006/0266132 | A1 | 11/2006 | Cheng et al. | |
| 2011/0116092 | A1 * | 5/2011 | Wang | G01N 15/0266 |
| | | | | 356/335 |
| 2013/0060509 | A1 | 3/2013 | Tsunoda | |

OTHER PUBLICATIONS

GB Search Report for GB Application No. GB1310759.4 dated Nov. 20, 2013.
Flagan, R.C., "History of Electrical Aerosol Measurements", Aerosol Science and Technology, vol. 28, No. 4, pp. 301-380 (1998).

\* cited by examiner

METHOD FOR OBTAINING AEROSOL PARTICLE SIZE DISTRIBUTIONS

CROSS REFERENCE TO RELATED APPLICATIONS

This application is a national stage filing under section 371 of International Application No. PCT/EP2014/062761, filed on Jun. 17, 2014, and published in English on Dec. 24, 2014 as WO 2014/202632 A1, which claims priority to Great Britain Patent Application No. 1310759.4, filed on Jun. 17, 2013, the entire contents of said applications being hereby incorporated herein by reference.

This invention relates to a method for obtaining aerosol particle size distributions. More particularly, the invention relates to a method that enables selection of monodisperse aerosol particles from a polydisperse particle ensemble in a wider particle size range.

BACKGROUND OF THE INVENTION

There is currently a great deal of concern about the health effects of nano-particles and micro-particles emitted unintentionally into the air. For example, a considerable increase in respiratory illness and allergies in the UK in recent years has been associated in part with particles emitted by diesel engines and other combustion processes. Whilst the main focus has been on diesel emissions, attention is turning to other potential sources such as power generation using fossil fuels, incineration, nuclear power generation and aircraft emissions. All heavy industries involving processes emitting fumes have potential problems with the emission of aerosol particles. Such processes include smelting, firing, glass manufacture, welding, soldering, nuclear power generation and incineration. There is also concern amongst consumer companies that use of enzymes in washing powders, powder coatings and fibres used in disposable nappies and other products could cause problems. In addition, the US EPA is becoming increasingly concerned about gasoline engine emissions.

Nano-particles and nano-objects are known to produce toxic effects. For example, they can cross the blood-brain barrier in humans and gold nano-particles can move across the placenta from mother to fetus. Early studies with PTFE (polytetrafluoroethylene) particles around 20 nm in diameter showed that airborne concentrations of a supposedly inert insoluble material lower than 50 μg/$m^3$ could be fatal to rats.

In addition to concerns from a health perspective, the elimination or control of airborne particles is important in maintaining standards in the many thousands of clean rooms in the micro-electronics, pharmaceutical, medical, laser, and fibre optics industries.

Small particles can be classified as shown in Table 1 below.

TABLE 1

| Term | Aerodynamic Equivalent Particle Size Range (dp = particle size) |
|---|---|
| Dust | dp > 10 μm |
| Coarse particles | 2.5 μm < dp < 10 μm |
| Fine particles | 100 nm < dp < 2.5 μm |
| Nano-particles or ultrafine particles | 1 nm < dp < 100 nm |

The term "nano-particles" is used to refer to particles having an aerodynamic particle size in the range from 1 nm to 0.1 μm.

For spherical particles, the aerodynamic particle size is the geometric diameter of the particle. Real particles in the air often have complicated shapes. For non-spherical particles, the term "diameter" is not strictly applicable. For example, a flake or a fibre has different dimensions in different directions. Particles of identical shape can be composed of different chemical substances and have different densities. The differences in shape and density cause considerable confusion in defining particle size.

The terms "aerodynamic particle size" or "aerodynamic diameter" are therefore used in order to provide a single parameter for describing real non-spherical particles having arbitrary shapes and densities. As used herein, the term "aerodynamic diameter" is the diameter of a spherical particle having a density of 1 g/$cm^3$ that has the same inertial property (terminal settling velocity) in the air (at standard temperature and pressure) as the particle of interest. Inertial sampling instruments such as cascade impactors enable the aerodynamic diameter to be determined. The term "aerodynamic diameter" is convenient for all particles including clusters and aggregates of any forms and density. However, it is not a true geometric size because non-spherical particles usually have a lower terminal settling velocity than spherical particles. Another convenient equivalent diameter is the diffusion diameter or thermodynamic diameter which is defined as a sphere of 1 g/$cm^3$ density that has the same diffusivity in air as a particle of interest.

The investigation and monitoring of aerosol particles in the atmosphere has been hampered by a shortage of instruments which can measure in the wide particle size range but which are sufficiently inexpensive, robust and convenient to be used on a widespread basis.

Instruments for measuring and selecting aerosol particles can be based upon the electrical mobility of the particles; see for example: Flagan, R. C. (1998): History of electrical aerosol measurements, *Aerosol Sci. Technol.,* 28(4), pp. 301-380. One such instrument is a Differential Mobility Particle Sizer (DMPS) which can be used to determine the size distribution of particles in an aerosol. A DMPS consists of a Differential Mobility Analyzer (DMA), which transmits only particles with a certain size, and a Condensation Particle Counter (CPC), which counts the particles.

A Differential Mobility Analyzer typically comprises a chamber having an inlet and an outlet for an aerosol gas sample and an inlet and an outlet for clean carrier gas ("sheath air" or "sheath gas") which carries the aerosol gas sample along the chamber. The chamber contains a pair of electrodes of opposing polarities towards which charged particles in the aerosol sample are attracted. In some DMA devices, a concentric electrode arrangement is used in which a rod-like electrode is arranged along the centre of the chamber and a cylindrical outer wall of the chamber functions as the other electrode. In other DMA devices, the electrodes can be a pair of opposed electrode plates.

In use, the aerosol sample is introduced into the chamber through the inlet and is carried along the chamber by the sheath air towards the aerosol gas outlet. As the aerosol passes along the chamber, charged particles in the aerosol are attracted towards one or other of the electrodes. The extent to which the path of the charged particles deviates from a line between the aerosol inlet and aerosol outlet will depend on the electrical mobility of the particles, the potential applied to the electrodes and the flow rate of the sheath air. The electrical mobility of the particles is a function of the size of the particle and its charge. Thus, at a given electrode potential, particle charge and sheath air flow rate, smaller particles will be attracted more readily to an electrode than larger particles. Therefore, by varying the potentials of the electrodes, it is possible to select which size fraction of the aerosol sample is allowed to reach the aerosol outlet. By varying the potentials at the electrodes and repeating measurements at each potential, it is possible to obtain a particle size distribution for the aerosol.

The particles present in aerosol samples taken from the atmosphere or elsewhere will typically contain both charged and uncharged particles in random and unknown proportions. Therefore, prior to entering the chamber, the aerosol gas sample is generally passed through a charging device which imparts a charge to the neutral particles in the aerosol and re-charges or adjusts the charge of particles in the aerosol that are already charged. The charging device is set up to apply a predetermined and consistent charge to the particles.

Normally, a DMA can be used to measure particle sizes of up to about 500 nm or sometimes, by using a longer DMA column, particles having a size up to about 1,000 nm. However, in many practical situations, it is necessary or desirable to measure particles whose sizes may range from a few nanometers up to ten micrometers (defined as $PM_{10}$). In this wide range, the mobility of the particles varies over several orders of magnitude and, in practice, it is extremely difficult to measure such wide ranges of particle sizes using a single DMA device.

It would undoubtedly be advantageous to be able to measure particle size distributions over a wide range of particle sizes and attempts have been made to solve this problem by carrying out the measurement using two devices, namely an electric mobility analyzer and an impactor. The electric mobility analyzer is first used to measure the size distribution of small particles and then the aerosol is directed to an impactor to determine the size distribution of larger particles. An example of this approach is disclosed in U.S. Pat. No. 7,140,266. U.S. Pat. No. 7,140,266 describes a device in which an electric mobility analyzer and an impactor are connected to each other in such a way that the bottom plate of the mobility analyzer is simultaneously used as the inlet part of the impactor. However, the device of U.S. Pat. No. 7,140,266 suffers from several potential drawbacks. Firstly, the device requires a large pump for the impactor which means that the device would be difficult to build as a portable instrument. Secondly, a cascade impactor classifies particles according to their aerodynamic diameters which may differ from their diffusion diameters, and consequently, the particle size distributions obtained by combining the results obtained from the impactor and the DMA may be rather difficult to interpret.

US 20060266132 discloses a multi-stage differential mobility analyzer for aerosol measurements which includes a first electrode or grid including at least one inlet or injection slit for receiving an aerosol including charged particles for analysis, and a second electrode or grid spaced apart from the first electrode. The second electrode has at least one sampling outlet disposed at a plurality of different distances along its length. A volume between the first and the second electrode or grid between the inlet or injection slit and a distal one of the plurality of sampling outlets forms a classifying region. At least one inlet or injection slit in the second electrode receives a sheath gas flow into an upstream end of the classifying region. Each sampling outlet functions as an independent DMA stage and classifies different size ranges of charged particles based on electric mobility simultaneously. The analyzer disclosed in US 20060266132 enables the measurable particle size range to be extended but a disadvantage is that the dimensions of the apparatus are necessarily increased, thereby mitigating against miniaturization and the construction of portable versions of the instrument.

Some of the problems involved in the measurement of larger particle sizes using differential mobility analyzers can be illustrated by reference to the schematic representation of a known type of DMA shown in FIG. 1.

FIG. 1 is a schematic side sectional view of a planar DMA unit used in known types of scanning particle mobility sizer (SMPS) apparatus. The DMA comprises a chamber having a sheath gas inlet 1 which is used to introduce a sheath gas flow into the DMA; a sheath gas outlet 2 for the sheath flow; an aerosol inlet 4; an aerosol outlet 5, and a pair of opposed electrodes 6 and 7 connected to a DC voltage supply. A flow maintaining system 3 comprising a pump and aerosol filters (not shown), and associated tubing 8 provide a steady flow of sheath gas through the chamber.

In operation, charged aerosol particles (preferably each having a single charge) are introduced into the DMA via the aerosol inlet 4 and move along the interior chamber of the DMA towards the end containing the aerosol outlet 5 and the sheath gas outlet 2. As a consequence of the voltage applied to the electrodes 6 and 7, the particles will be attracted towards the electrode 6, the extent of the attraction depending on the voltage and the electrical mobilities of the particles. At a given voltage and sheath gas flow, a proportion of the particles (particles having the same electrical mobility) will follow trajectory 9 and will pass out through aerosol outlet 5 from which they are directed to a CPC or electrometer where they are counted. By varying the voltage, particles having different electrical mobilities can be directed to the outlet 5. Because the electrical mobility of the particles is generally proportional to the size of the particles, it is possible to fractionate the aerosol particles according to size by varying the voltage applied to the electrodes 6 and 7. In general, the greater the size of the particles, the greater the voltage required to select particles and direct them to the outlet 5.

Differential mobility analyzers working on the above principles can be used very effectively to select particles of up to about 500 nm but, for larger particle sizes, problems do arise. In order to select particles of larger sizes, higher electrode voltages will be required and this places certain practical limits on the DMA. If the voltage is too high, corona discharges (or even complete electrical field breakdown) are likely to occur between the electrodes. This would be a particular problem for DMA devices with relatively narrow gaps between the electrodes (for example in miniaturized or portable devices).

An alternative to increasing the electrode voltage is to increase the length of the DMA chamber but this would lead to DMA chambers of impractical length and would further militate against miniaturization and the construction of portable hand-held DMA devices.

A further alternative to increasing the electrode voltage or increasing the length of the DMA chamber would be to reduce the flow rate of the sheath gas thereby enabling each particle to spend more time in the electric field. However, reducing the flow rate will also allow more time for the particles to undergo random movement by diffusion thereby leading to poorer resolution. This is illustrated by FIG. 2 below which is a schematic view of aerosol particle size distributions obtained at various sheath flow rates. In FIG. 2, the solid line corresponds to a size distribution obtained at a higher sheath flow rate $Q_{sh1}$ and the dashed line represent a size distribution obtained for the same aerosol but with a lower sheath flow rate $Q_{sh2} < Q_{sh1}$. At the lower sheath flow rate, the observed size distribution is significantly greater and less well defined than the size distribution obtained at the higher sheath flow rate.

At present, therefore, there remains a need for a method of obtaining aerosol particle size distributions in a wide range of particle sizes using a stand-alone DMA device or a DMA as part of an SMPS device, and in particular a method which can be carried out using a miniaturised or portable SMPS device.

SUMMARY OF THE INVENTION

The present invention sets out to provide a method of aerosol particle quantification that can be used with a size distribution quantifying apparatus, e.g. a portable scanning mobility particle sizer (SMPS) apparatus over a wide range of particle sizes.

In a first aspect, the invention provides a method for obtaining aerosol particle size distributions with a scanning mobility particle sizer (SMPS) device comprising a differential mobility analyzer (DMA); which method comprises the stages:

(i) collecting a first data set of particle concentrations vs. size for a size range from a predetermined minimal size $D_{min}$ to an intermediate size $D_t$ by varying a voltage applied to a DMA column of an SMPS from $V_{min}$ to $V_{t1}$ at a first sheath flow rate $Q_{sh1}$;

(ii) changing the sheath flow rate from the first sheath flow rate $Q_{sh1}$ to a second sheath flow rate $Q_{sh2}$;

(iii) collecting a second data set of particle concentrations vs. size for a size range from the intermediate size $D_t$ to a predetermined maximum size $D_{max}$ by varying the voltage applied to the DMA column of the SMPS from $V_{t2}$ to $V_{max}$ at the second sheath flow rate $Q_{sh2}$;

(iv) convolving the first data set from stage (i) using an apparatus function of the DMA and the sheath flow rates $Q_{sh1}$ and $Q_{sh2}$ in stage (ii);

(v) combining the convolved data set from stage (iv) with the second data set from stage (iii) to form a merged data set corresponding to the size distribution from $D_{min}$ to $D_{max}$; and (vi) deconvolving the merged data set to provide a size distribution for the full size range $D_{min}$ to $D_{max}$.

Thus, according to the method of the invention, a first data set of particle concentrations vs size is obtained for a size range from a predetermined minimal size $D_{min}$ to an intermediate size $D_t$ by varying the voltage applied to the DMA column from $V_{min}$ to $V_{t1}$ at a first sheath flow rate $Q_{sh1}$.

The intermediate size $D_t$ (which may also be referred to herein as the "transition size") is typically the largest size (or close to the largest size) that can be recorded with an SMPS at the initial flow rate $Q_{sh1}$.

After the first data set has been collected, the sheath flow rate is changed from the first sheath flow rate $Q_{sh1}$ to a second (typically lower) sheath flow rate $Q_{sh2}$ and a second data set of particle concentrations vs. size is collected for a size range from the intermediate size $D_t$ to a predetermined maximum size $D_{max}$ by varying the voltage applied to the DMA column of the SMPS from $V_{t2}$ to $V_{max}$.

The reduction in the sheath flow rate means that there is time for diffusion of particles to take place with the result that the apparent size distribution measured at the lower sheath flow rate is wider than the actual particle size distribution. In addition, the width of a peak is influenced by the ratio of the sheath and aerosol flows. This ratio affects the spread of particle trajectories in the DMA. The extent of this "peak spreading" or loss of resolution is determined by the "apparatus function" of the DMA which is an inherent property of the apparatus and will depend upon inter alia the geometry and size of the chamber containing the electrodes and aerosol and sheath gas inlets and outlets. The apparatus function can be determined at the factory before the DMA/SDMS apparatus is despatched to a customer, or it can be determined subsequently by calculation or by empirical means. One method of determining the apparatus function is to calibrate the apparatus using a monodisperse aerosol of known particle size such as polystyrene latex (PSL) particles (e.g. 50 nm or 100 nm). By taking measurements at different sheath flow rates and comparing the apparent (i.e. observed) particle size distributions with the actual particle size, the apparatus function can be calculated according to known and standard methods, see for example Hinds W. C. (1999) Aerosol technology. Properties, behavior and measurement of airborne particles. N.-Y.: J. Wiley and Sons, pp. 233-259.

As an example, the apparatus function of a Naneum NPS500 instrument was determined using sheath flows of 3 l/min and 0.6 l/min and a monodisperse 50 nm sebacate aerosol: see FIG. 8 below.

In the method of the invention, the voltages $V_{t1}$ and $V_{t2}$ are chosen experimentally to enable continuity of sizes at the intermediate (or transition) particle size $D_t$. Thus the final size in the first data set should be equal to the first size in the second data set.

If the first and second sets of data are put together, the result is a corrupted distribution curve as shown in FIG. 4 below, the corruption of the curve resulting from the spreading effect of the apparatus function on the second set of data.

Therefore, in stage (iv) of the method, the first data set from stage (i) is convolved using the apparatus function of the DMA and the sheath flow rates $Q_{sh1}$ and $Q_{sh2}$ in stage (ii) so that when merged with the second data set in stage (v) a smooth composite size distribution curve is obtained: see FIG. 5 below. It will be appreciated that since the first data set has been "downgraded" by convolution, the observed size distribution in FIG. 5 will differ from the true size distribution.

Finally, in stage (vi) of the method of the invention, the merged data set is deconvolved to provide a substantially true size distribution for the full size range $D_{min}$ to $D_{max}$.

The terms "convolving" and "deconvolving" are used herein in their conventional mathematical sense. Methods for convolution and deconvolution of data sets are well known to the skilled person.

By using the method of the invention, an SMPS can be set up to measure particle size distributions from 3 nm to 4,000 nm, or from 5 nm to 1,000 nm without the need for lengthening of the DMA chamber or excessive increases in electrode voltage.

In another aspect, the invention provides a DMA and/or SMPS set up to perform the method of the invention.

In a further aspect of the invention, the method is applied to a Fast Mobility Particle Sizer (FMPS) to characterise aerosol particles.

Further aspects and features of the invention will be apparent from the specific embodiments described below and illustrated in FIGS. 1 to 9.

The solid line is the measured size distribution (dN/dLogD), with a false peak at 250 nm, and the dashed line is an improved distribution obtained using the method of the invention.

DETAILED DESCRIPTION OF THE INVENTION

The invention will now be illustrated in greater detail by reference to the specific embodiments described below and illustrated in the accompanying drawings FIGS. 1 to 9.

Figure 1:
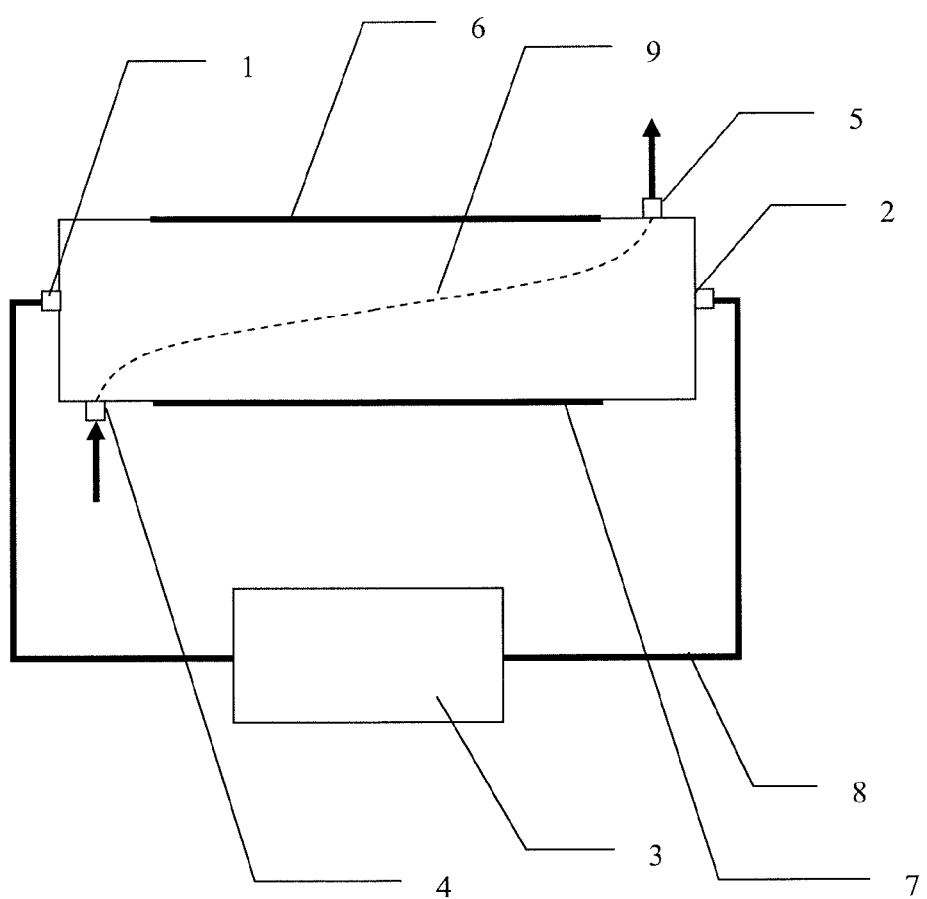
FIG. 1 is a schematic side sectional view of a known type of a planar DMA unit used in an SMPS apparatus.

FIG. 1 is a schematic side sectional view of a known type of a planar DMA unit used in SMPS apparatus and functions in the manner described above in the introduction section of this application. A schematic view of aerosol particle size distributions obtained at various sheath flow rates is shown in FIG. 2.

According to the invention, the apparatus shown in FIG. 1 (and other DMA/SMPS apparatuses) can be obtained with two different sheath flow rates changing at a transition size $D_t$. Initially, a part of the size distribution is recorded at a sheath flow rate of $Q_{sh1}$, see FIG. 3. The measurements extend from the lowest size to point A, which corresponds to the transition size $D_t$. At this point, the scan is stopped and the sheath flow rate is changed from $Q_{sh1}$ to a smaller value $Q_{sh2}$. At the smaller sheath flow rate, the number/size distribution is different (point B) from the distribution obtained at the higher sheath flow rate because of the effect of the apparatus function on the size distributions, as shown schematically in FIG. 2.

Figure 2:
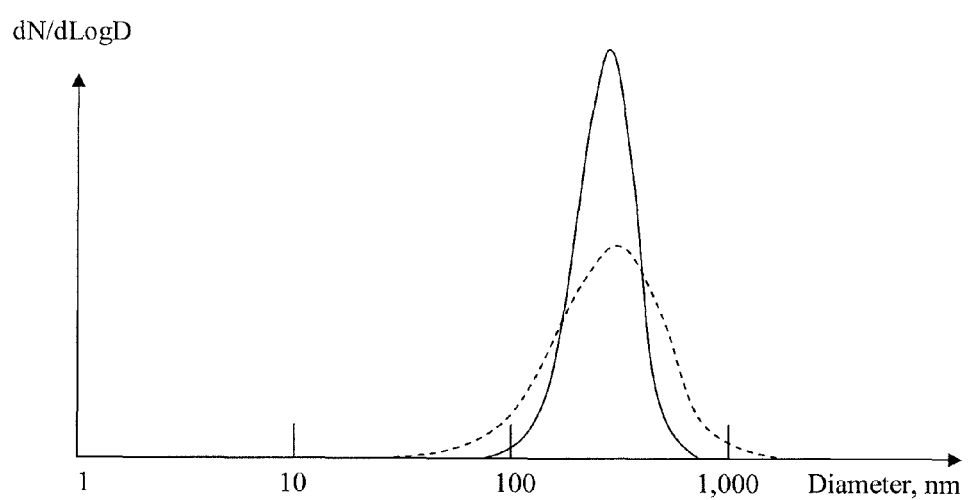
FIG. 2 is a schematic view of aerosol particle size distributions obtained at various apparatus functions corresponding to a higher sheath flow rate (solid line) and to a lower sheath flow rate (dashed line).
Figure 3:
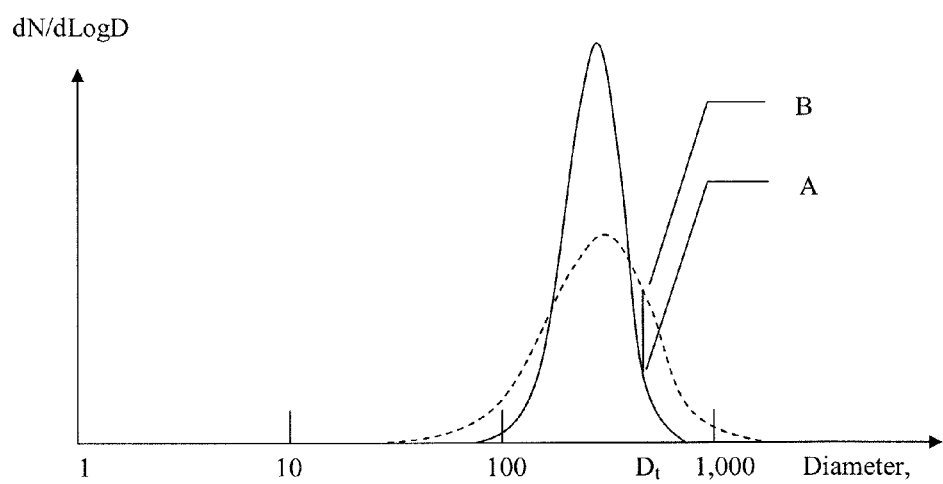
FIG. 3 is a schematic view of aerosol particle size distributions shown in FIG. 2 with a $D_t$ indicated by two lines between A and B.
Figure 4:
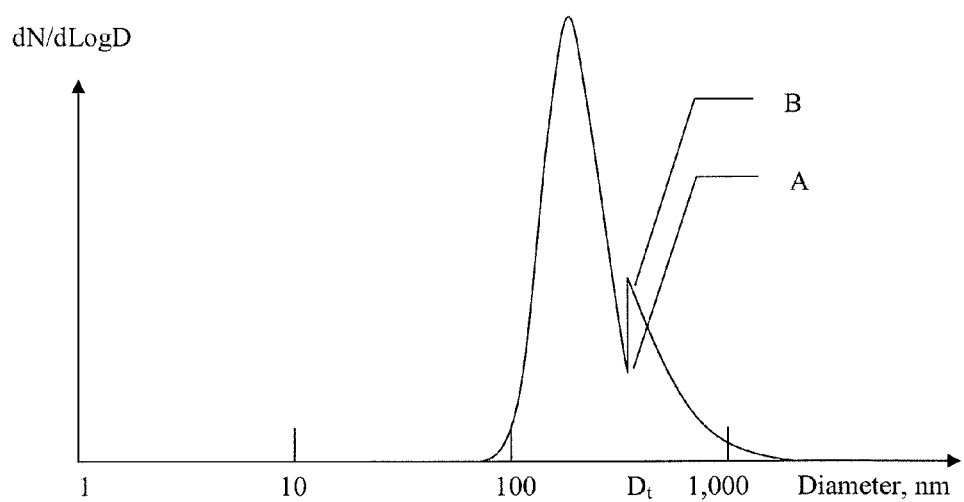
FIG. 4 is a schematic view of a raw aerosol particle size distribution obtained at two different flow rates changing from $Q_{sh1}$ to $Q_{sh2}$ at $D_t$.

In FIG. 2, the solid line corresponds to a size distribution obtained at a sheath flow rate $Q_{sh1}$ when the apparatus function is narrow, e.g. so narrow that it can be neglected. The dashed line represent a size distribution obtained for the same aerosol but with a lower sheath flow rate $Q_{sh2} < Q_{sh1}$. For the lower sheath flow rate $Q_{sh2}$, the apparatus function is wider and therefore it cannot be neglected because it affects the size distribution; i.e. it widens the distribution and thus reduces resolution. Ideally, it is preferable to obtain size distributions at the higher sheath flow ($Q_{sh1}$).

Changing the sheath flow rate in principle solves the problem of recording size distributions over a wider size range with a portable SMPS but it creates the further problem of the incompatibility of two parts of a size distribution obtained at different flow rates. A size distribution recorded in such a way is corrupted by the apparatus function of the part recorded at the lower sheath flow rate and may contain a false maximum, e.g. see FIG. 4.

Note that the second peak at $D_t$ is an artefact caused by changing the apparatus function; it is not a real aerosol distribution feature but a false peak.

The distortion of a size distributions obtained at different sheath flow rates is caused by the effect of apparatus functions on distribution. According to [Hinds W. C. (1999) Aerosol technology. Properties, behavior and measurement of airborne particles. N.-Y.: J. Wiley and Sons, pp. 233-259], a measured size distribution $f_m(D)$ is linked to the apparatus function A(D−Dv) as follows:

$$f_m(D) = \int_{D_{min}}^{D_{max}} f(Dv) \cdot A(D - Dv) \, dDv \qquad (1)$$

Here D is the particle diameter, Dv is the integral variable, $D_{max}$ and $D_{min}$ define the integration interval. The true distribution is $f(D)$. If the apparatus function is so narrow that its width can be neglected, then expression (1) is reduced to:

$$f_m(D) = f(D) \qquad (2)$$

Expression (2) enables the true distribution function $f(D)$ to be obtained directly from a measured distribution $f_m(D)$.

In practice, an aerosol particle number size distribution recorded with a portable apparatus at different flow rates contains two sub-distributions. One distribution is for small particles $D<D_t$ and the other is for larger particles $D>D_t$. It can be assumed that a true distribution or a distribution where the apparatus function is negligible is obtained at the highest sheath flow rate for $D<D_t$. The other distribution obtained at the lower sheath flow rate is widened by the apparatus function. One theoretically possible way of improving the quality of the size distributions would have been to deconvolve the second part of the size distributions recorded at $D<D_t$. Deconvolution can be carried out according to equation (1) using numerical techniques that are widely used and are well known to the skilled person. However, it was discovered that simply deconvolving part of a size distribution gave poor results and did not provide reliable data. For example, extra or deformed peaks were observed on many occasions.

Instead of just deconvolving the second part of the size distribution and combining it with the first distribution, the method of the invention (see references to Stages 4 and 5 above) involves convolving the first distribution ($D<D_t$) obtained at the higher sheath flow rate and then combining the convolved first distribution with the second distribution obtained for $D>D_t$.

Figure 5:
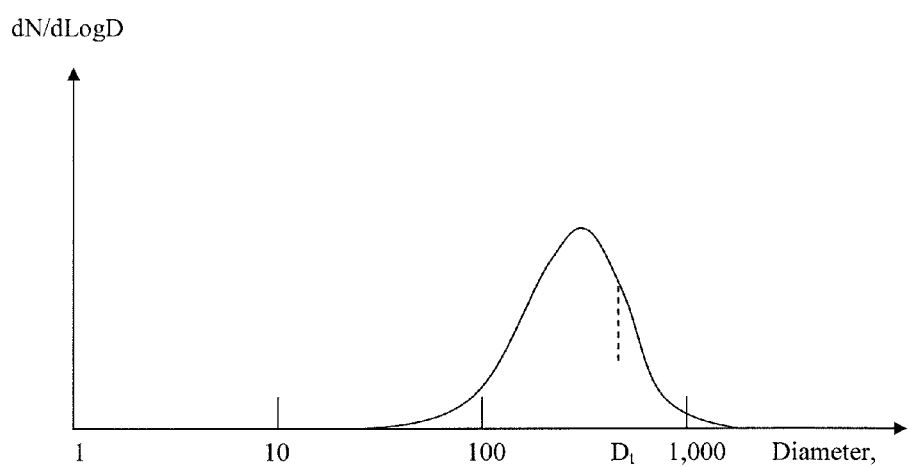
FIG. 5 is a schematic view of an aerosol particle size distribution obtained at two different flow rates changing from $Q_{sh1}$ to $Q_{sh2}$ at $D_t$ after convolution of the first data set and combining with the second data set (Stage 5 of the method).
Figure 6:
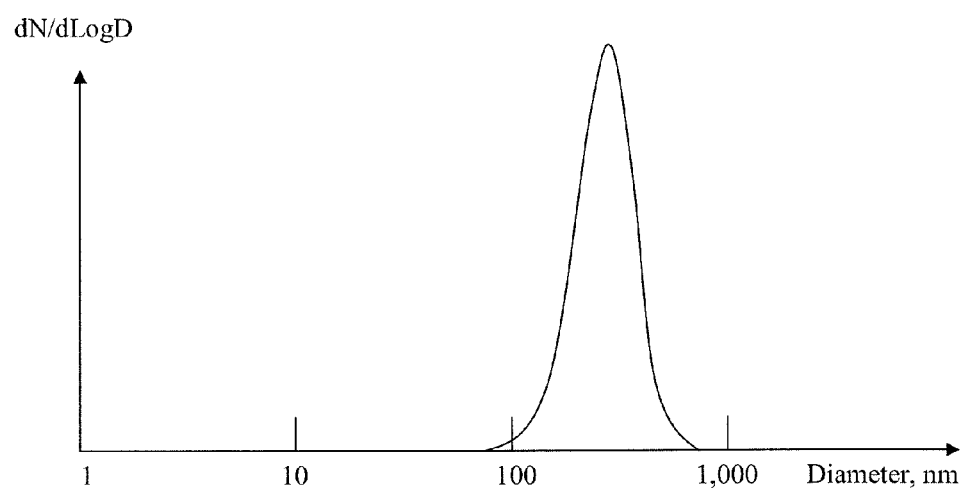
FIG. 6 is a schematic view of an aerosol particle size distribution after deconvolution at Stage 6.

The convolution step is a straightforward integration step and has been found to give very reliable results. After the convolution of the first distribution and combination of the convoluted first data set with the data set for the second distribution, an artificially (numerically) widened distribution is obtained as shown in FIG. 5. It will be appreciated that this distribution is reconstructed from two parts and represents a full distribution over a wide size range. The full distribution can be reliably deconvolved (Stage 6) and converted into the true distribution, see FIG. 6. A size distribution obtained in this way combined a high resolution distribution measured directly for smaller particles ($D<D_t$) and a high resolution distribution calculated in accordance with the present invention for larger particles ($D>D_t$).

Figure 7:
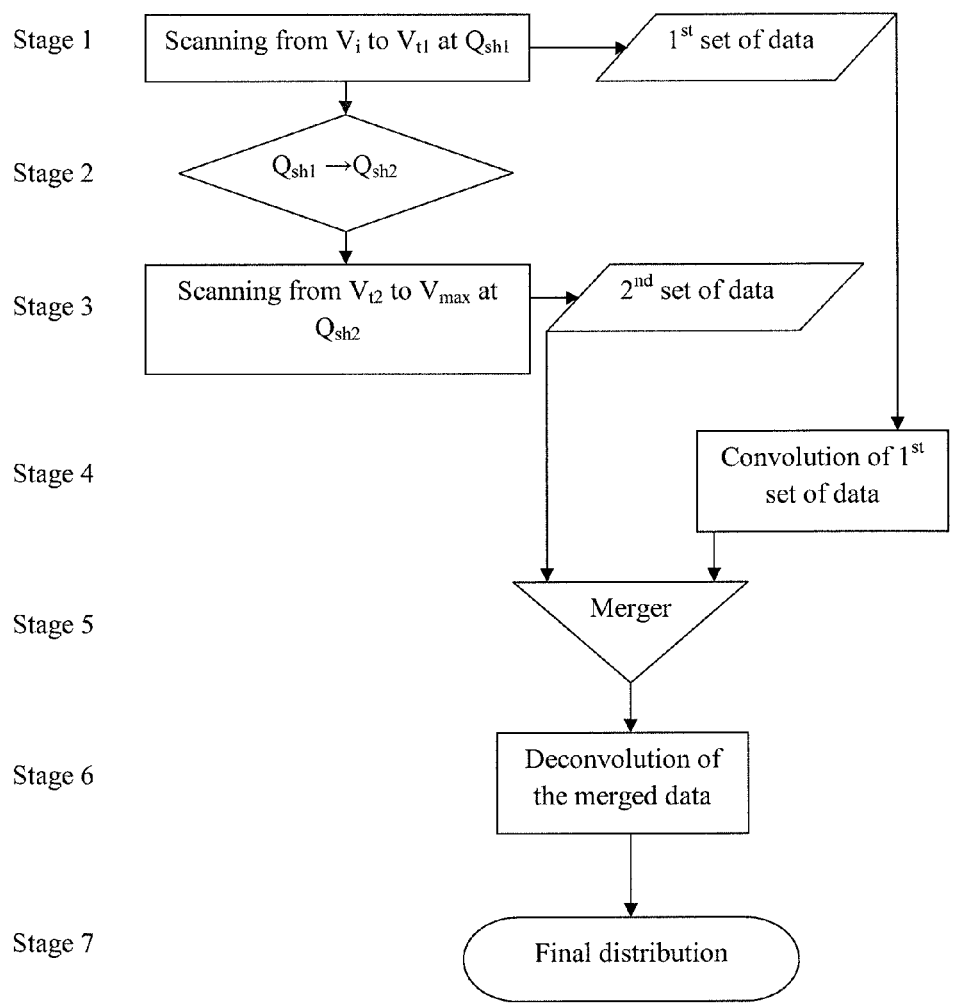
FIG. 7 is a block diagram showing the various stages in the method according to the invention.

The various stages involved in the method of the invention are shown schematically in the flow chart in FIG. 7.

Although the invention has been illustrated by reference to a method using a single intermediate (transition) size, a plurality of $D_t$ sizes and therefore sheath flow rates could be employed in the method to reconstruct and improve size distributions.

Figure 8:
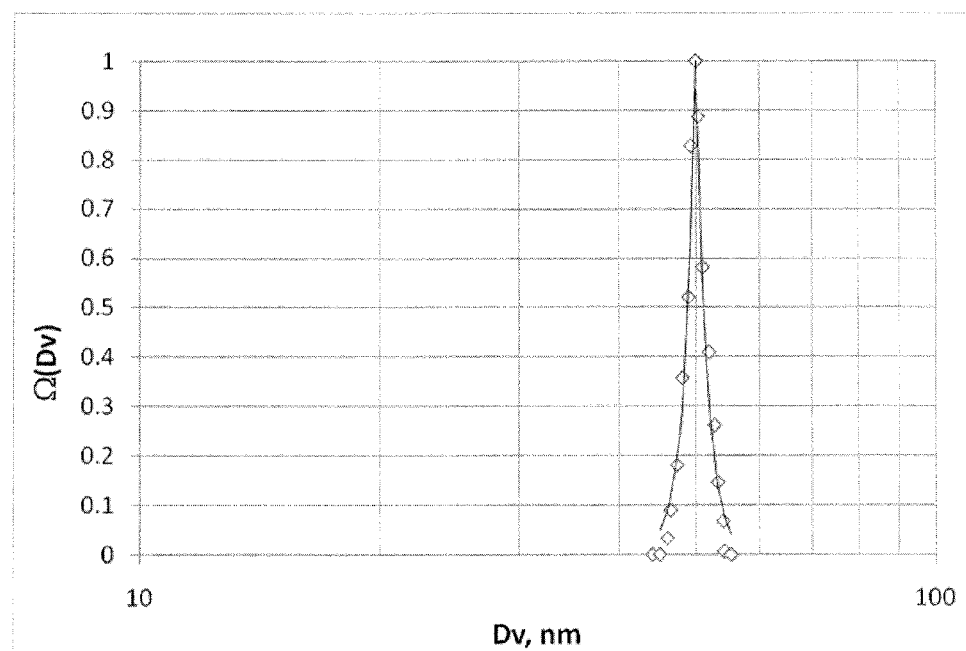
FIG. 8 is a typical apparatus function A(D−Dv) for the NPS500 (Naneum SMPS) instrument, obtained for D=50 nm.

An example of the apparatus function used in the method is shown in FIG. 8. The function was obtained for the Naneum NPS500 instrument with sheath flows of 3 l/min and 0.6 l/min. A monodisperse 50 nm aerosol was used. The apparatus function obtained is close to the transfer function well known and described in many publications, see for example the ISO 19500 standard.

Figure 9:
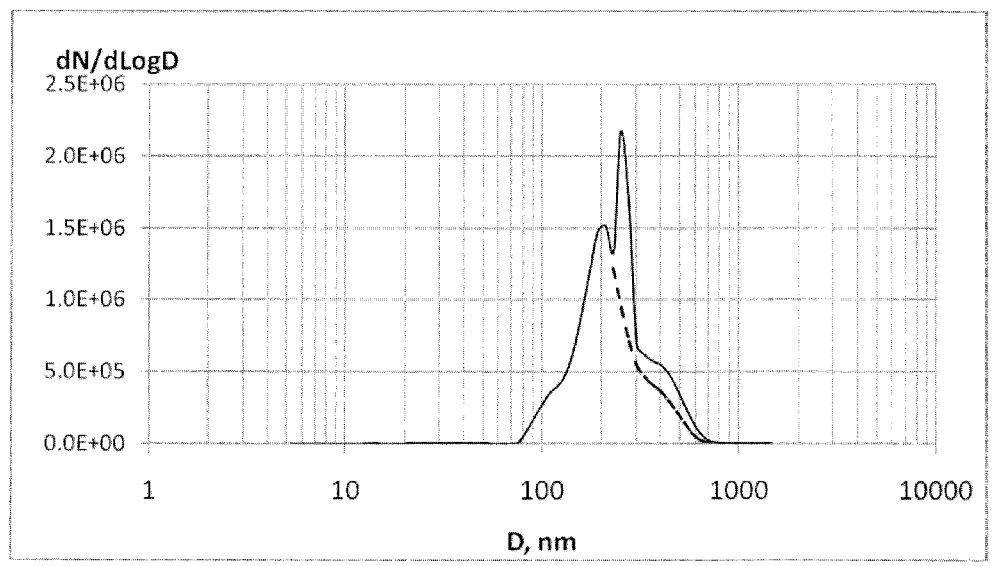
FIG. 9 is an illustration showing the effect of the method of the invention on the size distributions of a sebacate aerosol obtained with an NPS500 (Naneum SMPS) instrument.

FIG. 9 is an illustration showing the effect of the method of the invention on the size distributions of a sebacate aerosol obtained with an NPS500 (Naneum SMPS) instrument. The solid line represents the combination of the size distributions (dN/dLogD) obtained with two different sheath flows. It has two peaks at 200 nm and 250 nm. The aerosol was a mono-modal aerosol with a maximum at 200 nm. Therefore, the second peak at 250 nm is not real but a false peak. The method shown in FIG. 7 and described above was applied to the data and a portion of the size distribution at $D>D_t$ was improved with the result that the false peak has disappeared.

The apparatus function A(D, Dv) can be approximated with two exponential functions, for example at Dv<D, A(D, Dv)=exp[−C(D−Dv)] and for Dv>D, A(D, Dv)=exp[−C(−D+Dv)] where D is the particle diameter, Dv is the integral variable (see expression 1) and C is a parameter found during quantification of the apparatus function. The parameter C can be found experimentally in way that should be known to anyone skilled in the art. Normally C is found in minimization of the difference between the measured apparatus function and calculated from the above expression.

The choice of flow rates, including the flow rates of the aerosols and the sheath flow rates (e.g. $D_t$) to be used in the method will differ from one instrument to another and will be governed by the geometry of the DMA and the parameters of the SMPS. Normally these can be chosen by routine trial and error.

EQUIVALENTS

It will readily be apparent that numerous modifications and alterations may be made to the specific embodiments of the invention described above without departing from the principles underlying the invention. All such modifications and alterations are intended to be embraced by this application.

The invention claimed is:

1. A method for obtaining aerosol particle size distributions with a scanning mobility particle sizer (SMPS) device comprising a differential mobility analyzer (DMA); which method comprises the stages:
   (i) collecting a first data set of particle concentrations vs. size for a size range from a predetermined minimal size $D_{min}$ to an intermediate size $D_t$ by varying a voltage applied to a DMA column of an SMPS from $V_{min}$ to $V_{t1}$ at a first sheath flow rate $Q_{sh1}$;
   (ii) changing the sheath flow rate from the first sheath flow rate $Q_{sh1}$ to a second sheath flow rate $Q_{sh2}$;
   (iii) collecting a second data set of particle concentrations vs. size for a size range from the intermediate size $D_t$ to a predetermined maximum size $D_{max}$ by varying the voltage applied to the DMA column of the SMPS from $V_{t2}$ to $V_{max}$ at the second sheath flow rate $Q_{sh2}$;
   (iv) convolving the first data set from stage (i) using an apparatus function of the DMA and the sheath flow rates $Q_{sh1}$ and $Q_{sh2}$ in stage (ii);
   (v) combining the convolved data set from stage (iv) with the second data set from stage (iii) to form a merged data set corresponding to the size distribution from $D_{min}$ to $D_{max}$; and
   (vi) deconvolving the merged data set to provide a size distribution for the full size range $D_{min}$ to $D_{max}$.

2. A method according to claim 1 wherein the first sheath flow rate $Q_{sh1}$ is higher than the second sheath flow rate $Q_{sh2}$.

3. A method according to claim 1 wherein the SMPS is set up to measure particle size distributions from 3 nm to 4,000 nm.

4. A method according to claim 1 wherein the SMPS is set up to measure particle size distributions from 5 nm to 1,000 nm.

5. A DMA and/or SMPS apparatus set up to perform the method of claim 1.

6. A Fast Mobility Particle Sizer (FMPS) apparatus set up to perform the method of claim 1.

7. A method according to claim 2 wherein the SMPS is set up to measure particle size distributions from 3 nm to 4,000 nm.

8. A method according to claim 2 wherein the SMPS is set up to measure particle size distributions from 5 nm to 1,000 nm.

* * * * *